United States Patent [19]

Ahluwalia

[11] Patent Number: 5,444,090

[45] Date of Patent: Aug. 22, 1995

[54] METHOD OF REDUCING THE RATE OF HAIR GROWTH

[76] Inventor: Gurpreet S. Ahluwalia, 8632 Stable View Ct., Gaithersburg, Md. 20879

[21] Appl. No.: 212,584

[22] Filed: Mar. 11, 1994

Related U.S. Application Data

[63] Continuation-in-part of Ser. No. 788,168, Nov. 5, 1991, abandoned.

[51] Int. Cl.⁶ ............... A61K 31/225; A61K 31/195; A61K 31/19
[52] U.S. Cl. ................... 514/547; 514/554; 514/558; 514/565; 514/570; 514/571; 514/574; 514/562; 424/70.1
[58] Field of Search ............... 514/554, 565, 558, 574, 514/547, 570, 571, 562; 424/70, 71, 72

[56] References Cited

U.S. PATENT DOCUMENTS

| | | | |
|---|---|---|---|
| Re. 29,814 | 12/1978 | Snyder | 424/81 |
| 3,426,137 | 2/1969 | Philpitt | 424/330 |
| 4,039,669 | 8/1977 | Beyler et al. | 424/243 |
| 4,139,638 | 2/1979 | Neri et al. | 424/324 |
| 4,161,540 | 7/1979 | Neri et al. | 424/324 |
| 4,191,775 | 3/1980 | Glen | 424/304 |
| 4,269,831 | 5/1981 | Ferrari et al. | 424/241 |
| 4,344,941 | 8/1982 | Wiechert et al. | 424/243 |
| 4,370,315 | 1/1983 | Greff et al. | 424/94 |
| 4,439,432 | 3/1984 | Peat | 424/240 |
| 4,701,322 | 10/1987 | Dixon et al. | 424/70 |
| 4,720,489 | 1/1988 | Shander | 514/171 |
| 4,885,289 | 12/1989 | Breuer et al. | 514/170 |
| 5,095,007 | 3/1992 | Ahluwalia | 514/23 |
| 5,096,691 | 3/1992 | Ahluwalia et al. | 514/380 |
| 5,132,293 | 7/1992 | Shander et al. | 514/46 |
| 5,143,925 | 9/1992 | Shander et al. | 514/378 |
| 5,271,942 | 12/1993 | Heverhagen | 424/451 |

FOREIGN PATENT DOCUMENTS

| | | |
|---|---|---|
| 0446699 | 9/1991 | European Pat. Off. . |
| 0532219 | 3/1993 | European Pat. Off. . |
| 1458349 | 12/1976 | United Kingdom . |

OTHER PUBLICATIONS

Messenger, The Journal of Investigative Dermatology, vol. 101, No. 1, Supplement, Jul. 1993, pp. 4S-9S.
Sato, Biology and Disease of the Hair, 1975, pp. 3-13.
Simpson et al., British Journal of Dermatology, (1979) 100, 687-692.
Burdick et al., Br. J. Derm. (1970) 82, Supplement 6, pp. 19-25.
Goos et al., Arch. Dermatol. Res. (1982) 273:333-341.
Girard et al., Arch. Dermatol. Res. 269, 281-290 (1980).
Champion, The Medical Journal of Australia, vol. 149, No. 4, Aug. 15, 1988, pp. 203-213.
Cooney et al., Int. J. Biochem., vol. 11, pp. 519-539 (1980).
Chase et al., Physiological Zoology, vol. XXIV, Jan. 1951, No. 1.
DeYoung et al., Cancer Research, 38:2697-3701, Nov. 1978.
Richards et al., Cancer Research, 42:4143-4152, Oct. 1982.
Jayaram et al., Biochem Pharmac., 24, pp. 1787-1792 (1975).

*Primary Examiner*—Marianne M. Cintins
*Assistant Examiner*—M. Moezie
*Attorney, Agent, or Firm*—Fish & Richardson

[57] ABSTRACT

The rate and character of mammalian hair growth is altered by the topical application to the skin of a composition containing an organic inhibitor of the enzyme L-asparagine synthetase.

19 Claims, No Drawings

METHOD OF REDUCING THE RATE OF HAIR GROWTH

This application is a continuation-in-part of U.S. Serial No. 07/778,168, filed Nov. 5, 1991, now abandoned.

This invention relates to a method and composition for altering the rate and character of mammalian hair growth particularly androgen-stimulated hair growth, by topical application to the skin of a composition containing an inhibitor of the enzyme L-asparagine synthetase.

It has previously been proposed that the rate of hair growth, as well as the character of hair can be modified by topical application of inhibitors of certain enzymes such as inhibitors of 5-α-reductase or ornithine decarboxylase, or such antiandrogens as androgen receptor binding agents, as described in U.S. Pat. Nos. 4,720,489 and 4,885,289. Moreover, it has been theorized that certain other enzymes, including gamma glutamyl transpeptidase, are involved in various stages of hair follicle formation or of hair growth, but the relation between the various enzymes and the reactions which they control, as well as their effect upon each other and upon hair growth, has not been fully understood, as appears from Richards et al., Cancer Research, Vol. 42, 4143–4152 (1982) and DeYoung et al., Cancer Research, Vol. 38, 3697–3701 (1978); and Chase, Physiol. Zool. Vol. 24, 1–8 (1951).

I have now found that the rate and character of mammalian (including human) hair growth, particularly androgen-stimulated hair growth, can be modified by topical application to the skin of a composition containing an organic inhibitor of the enzyme L-asparagine synthetase. Inorganic inhibitors such as zinc chloride are undesirable because they tend to be irritants.

Inhibitors of L-asparagine synthetase are molecules that bind to or chemically alter a specific site on the enzyme to inhibit the action of the enzyme. There are two types of inhibitors, irreversible and reversible. Reversible inhibitors can either be competitive or non-competitive. Irreversible organic inhibitors of L-asparagine synthetase are preferred for use in the invention. Inhibitors of L-asparagine synthetase do not include general protein denaturing agents like fatty acids, or metals that chelate non-specifically with various enzymes.

Among the organic inhibitors of the enzyme L-asparagine synthetase which can be used in the present invention are: guanidinosuccinic acid; oxaloacetic acid; L-cysteinesulfinic acid; diethyl aminomalonate; dipeptides containing L-aspartic acid (L-aspartylglycine, L-aspartyl-L-leucine, L-aspartyl-L-phenylalanine, L-aspartyl-L-proline, L-α-aspartyl-L-serine and L-α-aspartyl-L-valine); N-o-nitrophenylsulfenyl-L-aspartic acid; N-o-nitrophenylsulfenyl-L-glutamine; S-adenosyl-L-methionine; L-homoserine-β-adenylate; and ethacrynic acid. Of these, guanidinosuccinic acid, ethacrynic acid, oxaloacetic acid, L-cysteinesulfinic acid and diethyl aminomalonate are preferred.

The composition contains, in addition to the inhibitor, a non-toxic dermatologically acceptable vehicle or carrier which is adapted to be spread upon the skin. One such vehicle is disclosed in co-pending application PCT/U.S. 93/0506A, which is hereby incorporated by reference. The concentration of the inhibitor in the composition may be varied over a wide range, either in the form of a solution or dispersion, containing from 0.1 to 30% by weight of the inhibitor, preferably 2 to 15%, and the composition may be applied at a dosage rate of 10 to 25 mg/cm$^2$ of skin. That is, the dosage of inhibitor itself is from 10 to 7,500 μg per square centimeter of skin. Penetration enhancers may also be present in the composition, including alcohol, acetone, propylene glycol, polyethylene glycol, dimethyl sulfoxide, 2-pyrrolidone, N-methyl-2-pyrrolidone, surfactants, azone, and the like, preferably in an amount effective to cause at least 10% inhibition of hair growth when the composition is applied to the skin adjacent the hair. The maximum amount of composition effectively applied is limited by the rate at which the inhibitor penetrates the skin.

The composition should be topically applied to a selected area of the body where it is desired to inhibit hair growth. The unwanted hair growth which is inhibited may be normal hair growth or hair growth that results from an abnormal or diseased condition. Typically, the composition can be applied to the face, particularly to the beard area of the face, i.e., the cheek, neck, upper lip, and chin. The composition can also be applied to the legs, arms, torso or armpit. The composition is particularly suitable for inhibiting the growth of unwanted hair in women suffering from hirsutism. In humans, the composition should be applied once or twice a day, or even more frequently, for at least three months to achieve a perceived reduction in hair growth.

The following specific examples are intended to illustrate more clearly the nature of the present invention without acting as a limitation upon its scope.

Example 1

A vehicle or carrier was prepared having the following composition:

| Component | Percent concentration by weight |
| --- | --- |
| Water | 68% |
| Ethanol | 16% |
| Propylene Glycol | 5% |
| Dipropylene Glycol | 5% |
| Benzyl Alcohol | 4% |
| Propylene Carbonate | 2% |

To separate portions of the vehicle were added amounts of four different inhibitors of L-asparagine synthetase as shown in Table 1 and the pH was adjusted with sodium hydroxide to achieve complete dissolution.

Four groups (eight animals in each group) of male intact Golden Syrian hamsters were provided. These animals were considered acceptable models for human beard hair growth in that they display oval shaped flank organs, one on each side, each about 8 mm. in major diameter, which grow thick black and coarse hair similar to human beard hair. These organs produce hair in response to androgens in the hamster. The flank organs of each hamster were depilated by applying a thioglycolate-based chemical depilatory (Surgex), and to one organ of each animal was applied 10 μl of vehicle alone once a day, while to the other organ of each animal was applied an equal amount of vehicle containing inhibitor. After three weeks of such applications (five days a week), the flank organs were shaved and the amount of recovered hair (hair mass) from each was weighed. The extent of reduction in hair growth by the inhibitor was expressed as the percent decrease in hair mass on the organ treated with inhibitor as compared to the organ treated with vehicle alone. As a control, one group of eight animals had both flank organs of each animal treated with vehicle alone. This assay will be referred to herein as the "Golden Syrian hamster assay." The results were as shown in Table 1 below.

TABLE 1

Inhibition of Hair Growth by
Inhibitors of L-Asparagine Synthetase

| Treatment Group | Amount | pH | Hamster Flank Organ Hair Mass (mg.) | | Percent Inhibition |
|---|---|---|---|---|---|
| | | | Untreated Mean ± SEM | Treated Mean ± SEM | |
| Control (vehicle) | — | 7 | 1.92 ± 0.19 | 1.81 ± 0.24 | — |
| Guanidino-succinic acid | 6% | 7 | 1.48 ± 0.09 | 0.64 ± 0.07 | 57.1% |
| Oxaloacetic acid | 10% | 3–4 | 1.44 ± 0.18 | 0.77 ± 0.11 | 38.0% |
| Cysteine-sulfinic acid | 6% | 3–4 | 1.44 ± 0.16 | 1.10 ± 0.19 | 25.5% |
| Diethyl amino-malonate | 10% | 3–4 | 1.53 ± 0.18 | 1.18 ± 0.18 | 23.3% |

Example 2

Compositions were prepared containing 5%, 10%, and 20% respectively of guanidinosuccinic acid in the vehicle described in Example 1 above and applied as in that Example. The results were as shown in Table 2.

TABLE 2

Inhibition of Hair Growth by Guanidinosuccinic Acid

| Treatment Group | Amount | pH | Hamster Flank Organ Hair Mass (mg.) | | Percent Inhibition |
|---|---|---|---|---|---|
| | | | Untreated Mean ± SEM | Treated Mean ± SEM | |
| Control | — | 7 | 2.17 ± 0.24 | 1.78 ± 0.25 | — |
| Guanidino-succinic acid | 5% | 7 | 1.52 ± 0.19 | 0.69 ± 0.14 | 52.6 ± 8.2 |
| Guanidino-succinic acid | 10% | 7 | 1.86 ± 0.18 | 0.72 ± 0.19 | 55.7 ± 15.1 |
| Guanidino-succinic acid | 20% | 7 | 1.83 ± 0.31 | 0.38 ± 0.12 | 80.1 ± 5.8 |

It was found that similar topical treatments with a 10 and 20% solution of guanidinosuccinic acid (two treatments over a 24 hour period using groups of 10 animals) resulted in a respective 76 and 85% reduction of L-asparagine synthetase activity in the hamster hair follicles.

Example 3

Compositions were prepared containing 10% and 20% by weight of ethacrynic acid respectively in the vehicle described in Example 1 above, and applied to hamster flank organs under the same conditions as described in Example 1 except that seven animals were in each group instead of eight. The results are shown in Table 3 below.

TABLE 3

Inhibition of Hair Growth by Ethacrynic Acid

| Treatment Group | Amount | pH | Hamster Flank Organ Hair Mass (mg.) | | Percent Inhibition |
|---|---|---|---|---|---|
| | | | Untreated Mean ± SEM | Treated Mean ± SEM | |
| Control | — | 7 | 2.85 ± 0.26 | 2.82 ± 0.32 | — |
| Ethacrynic acid | 10% | 5 | 3.09 ± 0.27 | 1.82 ± 0.22 | 42% |
| Ethacrynic acid | 20% | 5 | 2.47 ± 0.27 | 0.91 ± 0.10 | 63% |

Similar results can be obtained using other organic inhibitors of L-asparagine synthetase.

What is claimed is:

1. A method of reducing the rate of mammalian hair growth which comprises
   selecting an area of mammalian skin from which a reduced rate of hair growth is desired; and
   applying a composition containing an effective amount of an organic inhibitor of L-asparagine synthetase to said area of mammalian skin, causing a reduction in the rate of hair growth from said area of mammalian skin.
2. The method of claim 1 in which said inhibitor is guanidinosuccinic acid.
3. The method of claim 1 in which said inhibitor is oxaloacetic acid.
4. The method of claim 1 in which said inhibitor is cysteinesulfinic acid.
5. The method of claim 1 in which said inhibitor is diethyl aminomalonate.
6. The method of claim 1 in which said inhibitor is ethacrynic acid.
7. The method of claim 1 in which said inhibitor is an irreversible inhibitor.
8. The method of claim 1 in which said inhibitor is a reversible inhibitor.
9. The method of claim 1 in which the concentration of said inhibitor in said composition is between 1% and 30%.
10. The method of claim 1 in which the composition is applied to the skin in an amount of from 100 to 3000 micrograms of said inhibitor per square centimeter of skin.
11. The method of claim 1 in which said mammalian skin is human skin and said area of human skin to which said composition is applied is an area of skin comprising beard hair.
12. The method of claim 1 in which said hair growth that is reduced is androgen-stimulated hair growth.
13. The method of claim 1 in which said composition, when tested in the Golden Syrian hamster assay, provides a reduction in hair growth of at least 23.3%.
14. The method of claim 1 in which said composition, when tested in the Golden Syrian hamster assay, provides a reduction in hair growth of at least 52.6%.
15. The method of claim 1, wherein said composition further includes a non-toxic dermatologically acceptable vehicle adapted to be spread on the skin.
16. The method of claim 1 in which said mammalian skin is human skin and said area of human skin to which said composition is applied is an area comprising leg hair.
17. The method of claim 1 in which said mammalian skin is human skin and said area of human skin to which said composition is applied is an area comprising arm hair.
18. The method of claim 1 in which said mammalian skin is human skin and said area of human skin to which said composition is applied is an area comprising armpit hair.
19. The method of claim 1 in which said mammalian skin is human skin and said area of human skin to which said composition is applied is an area comprising torso hair.

* * * * *

UNITED STATES PATENT AND TRADEMARK OFFICE
CERTIFICATE OF CORRECTION

PATENT NO.    : 5,444,090

DATED         : August 22, 1995

INVENTOR(S)   : Gurpreet S. Ahluwalia

It is certified that error appears in the above-identified patent and that said Letters Patent is hereby corrected as shown below:

On title page, item [56],

In the References Cited section, "5,096,691" should be --5,096,911--.

Signed and Sealed this

Ninth Day of July, 1996

Attest:

BRUCE LEHMAN

Attesting Officer

Commissioner of Patents and Trademarks